(12) United States Patent
Srinivas et al.

(10) Patent No.: US 11,077,421 B2
(45) Date of Patent: Aug. 3, 2021

(54) CARBON SORBENT FOR REMOVAL OF METAL CATALYSTS FROM PHARMACEUTICALS

(71) Applicant: TDA Research, Inc., Wheat Ridge, CO (US)

(72) Inventors: Girish Srinivas, Broomfield, CO (US); Steven Dietz, Englewood, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 46 days.

(21) Appl. No.: 16/128,293

(22) PCT Filed: Mar. 24, 2017

(86) PCT No.: PCT/US2017/023959
§ 371 (c)(1),
(2) Date: Sep. 11, 2018

(87) PCT Pub. No.: WO2017/172512
PCT Pub. Date: Oct. 5, 2017

(65) Prior Publication Data
US 2019/0099737 A1  Apr. 4, 2019

Related U.S. Application Data

(60) Provisional application No. 62/314,272, filed on Mar. 28, 2016.

(51) Int. Cl.
| | | |
|---|---|---|
| *B01J 20/20* | (2006.01) | |
| *B01J 20/28* | (2006.01) | |
| *B01J 20/30* | (2006.01) | |
| *C01B 32/30* | (2017.01) | |
| *C07C 67/34* | (2006.01) | |
| *C07C 67/56* | (2006.01) | |
| *C07C 201/12* | (2006.01) | |
| *C07C 201/16* | (2006.01) | |
| *C07D 209/42* | (2006.01) | |
| *B01D 15/00* | (2006.01) | |

(52) U.S. Cl.
CPC ......... *B01J 20/20* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28083* (2013.01); *B01J 20/305* (2013.01); *B01J 20/3078* (2013.01); *C01B 32/30* (2017.08); *C07C 67/34* (2013.01); *C07C 67/56* (2013.01); *C07C 201/12* (2013.01); *C07C 201/16* (2013.01); *C07D 209/42* (2013.01); *B01D 15/00* (2013.01); *B01J 2220/4825* (2013.01); *C01P 2006/12* (2013.01); *C01P 2006/14* (2013.01); *C01P 2006/16* (2013.01); *C01P 2006/80* (2013.01)

(58) Field of Classification Search
CPC .................................. B01J 20/20; C01B 32/30
See application file for complete search history.

(56) References Cited

U.S. PATENT DOCUMENTS

| | | | |
|---|---|---|---|
| 4,118,341 A * | 10/1978 | Ishibashi | C01B 32/318 502/433 |
| 7,541,312 B2 | 6/2009 | Dietz et al. | |
| 8,722,571 B2 * | 5/2014 | Bandosz | B01D 53/02 502/430 |
| 10,384,193 B2 | 8/2019 | Nguyen et al. | |

OTHER PUBLICATIONS

Food and Drug Administration Compliance Program Guidance Manual. Sep. 11, 2015. p. 4, definition of "active pharmaceutical ingredient".

* cited by examiner

*Primary Examiner* — Stuart L Hendrickson
(74) *Attorney, Agent, or Firm* — Brian J Elliott

(57) ABSTRACT

The present invention relates to a carbon sorbent the can selectively remove platinum-group metals and other heavy metals such as tin without co-removing organic synthesis products including pharmaceutical intermediates and finished Active Pharmaceutical Ingredients (APIs). The carbon sorbents of the present invention are made from low-cost, high purity starting materials and the resulting carbon sorbents are also very pure. The carbon sorbents possess a combination of certain nitrogen and phosphorous groups combined with mesoporosity (2 to 50 nm diameter pores) that proves the high metal adsorption.

3 Claims, 17 Drawing Sheets

CARBON SORBENT FOR REMOVAL OF METAL CATALYSTS FROM PHARMACEUTICALS

CROSS-REFERENCE TO RELATED APPLICATIONS

This application claims the benefit of U.S. Provisional Application No. 62/314,272, filed Mar. 28, 2016.

STATEMENT REGARDING FEDERALLY SPONSORED RESEARCH OR DEVELOPMENT

This invention was made using U.S. government funding through the U.S. Department of Health and Human Services, Food and Drug Administration, SBIR Contract Nos. R44FD004079-02 & 5RAAFD004079-03. The government has certain rights in this invention.

FIELD OF THE INVENTION

The present invention generally relates to carbon sorbents for removing metal catalysts from pharmaceuticals and intermediate compounds used to make pharmaceuticals. The metal catalysts may be palladium, platinum, tin or other transition metals or heavy metals. The present invention also relates to carbon sorbents for removing metal catalysts from the product of organic synthesis reactions.

BACKGROUND OF THE INVENTION

There is a need to remove toxic platinum-group elements, such as palladium as well as other toxic heavy metals including tin from pharmaceuticals. These platinum-group or heavy metals are used as catalysts in the drug's synthesis. While using sorbents is the typical method for isolating the drug from the metals, any purification step must also simultaneously minimize the loss of active pharmaceutical ingredients (API). New regulations to be enforced in the U.S. and Europe will require that Pd and Pt in the final API be limited to <5 ppmw (parts per million weight-basis) in oral medications and to <0.5 ppmw in non-oral (parenteral) medications. Chronic users of heavy-metal contaminated pharmaceuticals are especially susceptible to DNA damage in nerve-tissue, as the platinum-group elements are known to chelate especially strongly to the nitrogen-7 atom of guanine in DNA nucleotide pairs. These heavy metals also bind to the nitrogen of the other purine and pyrimidine bases, as well as to the phosphate backbone of DNA, all interfering with DNA transcription.

Toxic-metal contamination of pharmaceuticals arises from use of catalysts for drug synthesis, especially the platinum-group metals: Pt, Pd, Ru, Ir and Rh. Other neurotoxic metals, notably Sn, are non-catalytic but are used in stoichiometric quantities for certain reactions at very high concentrations and must also be removed. If catalytic metals used in early steps of drug synthesis are not removed from reaction mixtures between synthesis steps, they can also catalyze undesired side reactions in later steps, often producing toxic organic impurities that are similar in structure to the active pharmaceutical ingredients and that are extremely difficult to separate from the drug molecules.

It is estimated that ~80% of the pharmaceuticals synthesized today (2014) use Pd in at least one synthesis step. Some leading pharmaceuticals employing Pd as a catalyst in at least one synthetic step include: Lipitor (anti-cholesterol), Hydrocodone (pain relief), Lisinopril (blood pressure), Atenolol (blood pressure), Albuterol (asthma-oral), Ibuprofen (pain, arthritis), Celebrex (arthritis), Effexor XR (depression), Abilify (anti-psychotic), Crestor (anti-cholesterol) and Advair (asthma). The vast majority of pharmaceuticals are synthesized using at least one of the Pt-group elements in a catalytic step and especially Pd, Ru, Pt, Ir and Rh.

The cytotoxicity and neurotoxicity of Pt-group elements was widely recognized soon after introduction of the anti-cancer drugs, cis-platin and carboplatin. These compounds and analogs based on cis-palladium and other Pt-group metals bind strongly to DNA, especially to nitrogen of the nucleic acid, guanine, blocking transcription of critical neural enzymes. Like mercury and lead, Pd and the Pt-group metals strongly bind to the sulfhydryl group of the amino acid cysteine, found at the active sites of enzymes critical for energy utilization in the brain. Like lipophilic methyl mercury and tetraethyl lead, which are especially neurotoxic because they rapidly diffuse through lipid membranes of the nervous system, the organometallic coordination compounds used as homogeneous catalysts in drug manufacture are in fact specially designed with lipophilic ligands to enable solubility in the non-polar solvents used in drug synthesis. Although commercial adsorbents employing multi-dentate amine, phosphate and thiol functional groups bind Pt-group elements by displacing the more weakly-bound catalyst ligands, they are expensive (often $1000 to $2000·$kg^{-1}$) and more importantly, do not remove many Pt-group catalyst degradation products, cluster compounds and nano-suspensions. Although inexpensive commercial carbons remove many suspended species, they are not designed to selectively bind Pt-metals and can sorb unacceptably high quantities of aromatic drug, in addition to being sources of introducing new, unwanted impurities.

Some catalyzed pharmaceutical reactions may employ more than 6,000-8,000 ppmw Pd. Traditional methods of drug purification (extraction into solvents, crystallization or precipitation) are widely used but often leave unacceptably high residual levels of Pd or remove significant amounts of the valuable drug product or intermediate. This has led to development of adsorbents designed to strongly bind Pd to multi-dentate ligands containing O, N, S and P. Such functionalized adsorbents work well for removing Pd bound in complexes of active homogeneous catalysts that have labile ligands which are easily displaced. For compatibility with various solvents, functionalized adsorbents are available that are either polar (cellulose, silica, glass, alumina) or non-polar (polyethylene, polystyrene). Examples include ethylenediamine bound to polystyrene or silica, triethylamine bound to polyethylene or cellulose, thiourea bound to polystyrene, trimercaptotriazine bound to polystyrene, triamine-modified silica, amine-dicarboxylic acids bound to polystyrene, aminephosphoric acid on polystyrene, triphenylphosphine bound to polyethylene or cellulose, phosphine functionalized polystyrene, dithiothreitol bound to polystyrene, phosphotungstic acid-modified alumina and multi-dentate sulfur compounds on silica.

However, commercial adsorbents do not remove all metal species. For example, catalysts that have reached end of service life are often saturated with tightly-bound ligands which are not easily displaced. These include drug molecules, starting materials and intermediates that are often multi-dentate amines, nitrogen heterocycles, halides, and oxygenated compounds. Furthermore, atoms of Pt-group metals tend to cluster and nucleate colloidal particles with wide size distribution. Commercial carbons have been used with partial success for removing stable, bulky Pd complexes, Pd-cluster compounds, Pd nano-suspensions and colloidal suspensions. The greatest drawback of activated carbons is that they are not selective for Pd and can adsorb unacceptably large quantities of drug product (Garrett and Prasad 2004). What is needed is a sorbent that has high chemical affinity for the Pt-group metals (especially Pd) and will adsorb not only active homogeneous catalysts but also trap the entire range of catalyst degradation products—but without adsorbing active drug species.

Another problem with activated carbon sorbents is that they contain impurities. Typical activated carbons from natural precursors such as wood, coal and coconut shell can have impurities leftover from the starting material. Carbons produced from various types of biomass, coal or petroleum-based products may be contaminated with heavy metals or other toxic impurities making them unsuitable as sorbents in pharmaceutical production.

As such, there remains a need for a metal catalyst sorbent that can remove a large fraction of platinum-group metals as well as other toxic metals such as tin from pharmaceutical product mixtures, without co-adsorbing the valuable pharmaceutical compounds themselves. The sorbents described in the prior art suffer from at least one of the following limitations as it related to purifying pharmaceuticals: they have low purity, they contain toxic heavy metals, they contain other toxins, they do not selectively remove palladium, other platinum-group metals or other toxic heavy metals from pharmaceuticals (i.e. they also remove the valuable pharmaceutical or intermediate compounds) and/or they have a high cost.

BRIEF SUMMARY OF THE INVENTION

The present invention relates to a carbon sorbent the can selectively remove platinum-group metals and other heavy metals such as tin without co-removing organic synthesis products including pharmaceutical intermediates and finished APIs. The carbon sorbents of the present invention are made from low-cost, high purity starting materials and the resulting carbon sorbents are also very pure and contain very little impurities. Thus, the present invention solves the limitations of the prior art by. The key to the low cost of our carbons is that they are made primarily from carbohydrates such as sucrose, glucose, fructose, corn syrups and starches.

The present invention relates to carbon sorbents for removing metals from organic reaction products, the carbon sorbent comprising: a nitrogen content of at least 3 weight %, which is present in the form of pyridine, pyridone, pyrrole or N—P bonds, an oxygen content of between 7 weight % and 16 weight %, a phosphorous content of at least 0.8 atom % as measured by X-ray photoelectron spectroscopy, a BET surface area of between 200 and 1700 meters squared per gram, and a mesopore volume of at least 0.05 cubic centimeters per gram, wherein mesopores have a diameter of from 2 to 50 nm. The carbon sorbent may optionally have a pH of at most 5.0.more preferably at most 3.1. An optional embodiment of the carbon sorbents is an ash content of a most 1.0 weight %.

The carbon sorbents of the present invention are high purity and may have less than 0.1 atom % Na and less than 0.1 atom % K as measured by X-ray photoelectron spectroscopy.

In another embodiment, the carbon sorbents further comprise a platinum-group metal uptake of at least 83% from a solution of 1.3 ppm platinum-group metal in an organic solvent with an API product present in the organic solvent at a concentration of 1.0 grams of the API product per 0.5 grams of the carbon sorbent, and wherein recovery of the API product is greater than 99%. In a preferred embodiment the platinum-group metal is palladium.

In another embodiment, the carbon sorbent removes at least 90% of palladium from a solution containing a used palladium catalyst and an API product when the carbon sorbent is present at a relative concentration of 1.5 grams of the carbon sorbent to 1.0 grams of the API product, and wherein recovery of the API product is greater than 99%. Optionally, wherein the API product is the reaction product of a Suzuki reaction that was catalyzed by a palladium catalyst.

In another embodiment, the carbon sorbent removes at least 50% of palladium and at least 40% of tin from a solution containing a used palladium catalyst, a used tin stoichiometric reagent and an API product when the carbon sorbent is present at a relative concentration of 1.5 grams of the carbon sorbent to 1.0 grams of the API product. In an embodiment, the API product is the reaction product of a Stille reaction that was catalyzed by a palladium catalyst along with a stoichiometric tin reagent.

In another embodiment, the carbon sorbent removes at least 70% of ruthenium from a solution containing a used ruthenium catalyst and an API product when the carbon sorbent is present at a concentration of 1.5 grams of the carbon sorbent to 1.0 grams of the API product, and wherein recovery of the API product is greater than 99%. Optionally wherein the API product is the reaction product of a metathesis reaction that was catalyzed by a Grubb's first generation ruthenium catalyst.

In another embodiment, the carbon sorbent removes at least 90% of palladium from a solution containing a used palladium catalyst and a pharmaceutical intermediate product.

In a preferred embodiment, the carbon sorbent has a nitrogen content composed of at least 50 atom % of the nitrogen atoms of the carbon sorbent as pyridone/pyrrole groups, and at least 14 atom % of the nitrogen atoms of the carbon sorbent as pyridine groups, and optionally at least 20 atom % of the nitrogen atoms of the carbon sorbent are N—P bonded groups.

DETAILED DESCRIPTION OF THE INVENTION

Figure 1:
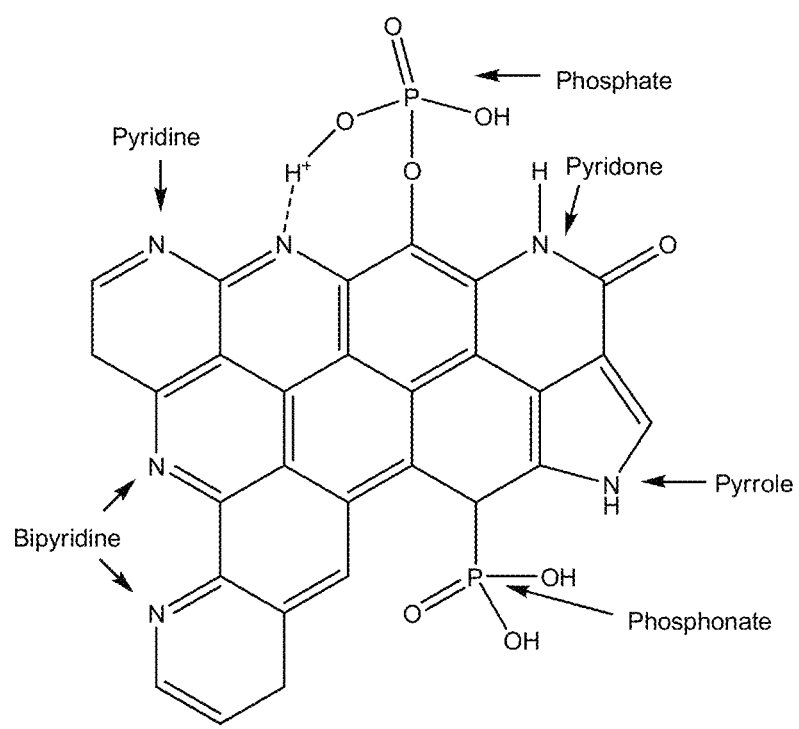
FIG. 1. Representative chemical structure of the carbon sorbents.

The summary of the invention above and in the Detailed Description of the Invention, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, and article "comprising" (or "which comprises") component A, B, and C can consist of (i.e. contain only) components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending on the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example 25 to 100 mm means a range whose lower limit is 25 mm, and whose upper limit is 100 mm.

The term, platinum-group metal, means ruthenium, rhodium, palladium, osmium, iridium, and platinum. The term, API, means Active Pharmaceutical Ingredient. The term "active pharmaceutical ingredient", or API, is intended to be the industry-recognized definition, stated by the U.S. FDA: An active pharmaceutical ingredient is "any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body."

The term, BET surface area, means Brunauer-Emmett-Teller surface area.

The term, mesopore volume, means the pore volume for all pores with an effective diameter of 2 to 50 nanometers. Pores are assumed to be round but other irregular shapes (for example slits) are to be understood.

The carbon sorbents of the present invention are both low cost and very pure because they are made from very low cost, high purity precursors using conventional processing methods. The key to the low cost of these carbons is that they are made primarily from carbohydrates such as sucrose, glucose, fructose, corn syrups and starches. The addition of specific nitrogen, phosphorous and oxygen structures in the carbon is controlled by the addition of high purity (di) ammonium phosphate and phosphoric acid to the carbohydrate precursors. The mixing, heating and activation steps lead to a material with high surface area, and a large volume of mesopores per gram of sorbent (mesopores have a diameter of 2 to 50 nm). These carbons have a very high affinity to adsorb platinum-group metal and tin and also have a low adsorption of pharmaceutical active compounds.

The carbon sorbents of the invention have a unique combination of properties including: a nitrogen content of at least 3 wt % in the form of pyridine, pyridone, pyrrole and N—P bonded groups; an oxygen content of at least 7 wt %; a carbon content of between 68 and 84 wt %; a phosphorous content of at least 1 wt %; a BET surface area of between 200 and 1700 m$^2$/g; a high amount of mesopores, specifically, a volume of mesopores from 2 to 50 nm of at least 0.05 cc/g or preferably between 0.075 and 0.6 cc/g, alternatively at least 0.1 cc/g. Another preferred embodiment is a mesopore volume of between 0.5 and 0.6 cc/g. In preferred embodiments, the carbon sorbents contain mesopores with a diameter of at least 10 nm, more preferably at least 20 nm. In other embodiments, the carbon sorbents also have a pH of between 2.0 and 6.0; a palladium removal of over 90%; a high purity including extremely low levels of trace heavy metals, less than 0.1 atom % contamination of Na or K, and an ash content of at most 1 wt %.

Unlike many commercial carbons produced from various types of biomass, coal and petroleum-based products, which are often contaminated with heavy metals and various other toxic impurities, the carbons of the present invention are formulated by carbonization of food-grade carbohydrates. Glucose and glucose released from acid-hydrolyzed cornstarch are preferred. Carbohydrates are a group of compounds that range in size from simple sugars to starch. Sugars are simple carbohydrates known as sugars including: sucrose, glucose, dextrose and maltose. Starch and cellulose are polymers of the glucose. Starch is a major constituent of potatoes, rice, beans, corn, wheat and peas. Cellulose is found in wood, grasses and cotton. Carbohydrates can be converted into carbon by pyrolysis.

Phosphoric acid, $H_3PO_4$ (available as food grade), hydrolyzes starch and phosphorylates the glucose monomers, acting as a cross-linking agent forming highly porous materials. To incorporate nitrogen ligands at graphitic edge sites and to make additional cross-links, $(NH_4)_2HPO_4$, or alternatively $(NH_4)H_2PO_4$, is added to the formulation. Nitrogen is incorporated into the carbonaceous edge sites and forms highly basic pyridinic, pyridonic and pyrrolic species that can strongly adsorb and chelate select complexes of palladium and other platinum-group metals, while less strongly adsorbing the alkaloidal pharmaceutical agents that are typically also rich in basic nitrogen. The phosphorus-rich starting materials are typically converted into metaphosphates and polyphosphates upon heating up to about 450° C. Upon further heating above 500° C., with 535° C. being preferred, the phosphates are partially reduced into phosphonates (phosphorus bound directly to carbon). The various phosphorus species also strongly bind platinum group metals, but remain acidic if not neutralized. The nitrogen and phosphorus functional groups at the graphitic edge sites roughly mimic those found in DNA.

We have produced a number of carbons with a broad range of elemental compositions and pore size distributions. Table 1 shows the formulations that have been made. For the carbohydrate, we looked at corn starch, dextrose, sucrose, fructose and combination of these. To enhance the metal binding to the carbon surface, we added nitrogen and sulfur containing compounds to the formulations. Nitrogen was added to the carbon using ammonium phosphate, urea, and melamine. Nitrogen and sulfur were incorporated using thiourea and ammonium sulfate, which contain both elements. The components were mixed and heated in air to 180° C. for 4 hours. The chars were then heated under nitrogen gas flow for 4 hours at 535° C. to form the carbon. They were then washed with distilled water to remove the residual phosphoric acid and dried at 110° C. In Table 1, the term "phosphate" under the heading ammonium compound means, preferably, diammonium phosphate, and alternatively ammonium phosphate. The abbreviation "phos" means "phosphate". Also, "carbonate" mean ammonium carbonate, "urea" means urea (with no ammonium component), "melamine" means melamine (with no ammonium component), "thiourea" means thiourea (with no ammonium component), and "sulfate" means ammonium sulfate.

TABLE 1

Carbon Formulations

| ID | Sugar Type | Sugar (wt %) | Ammonium Compound | Ammonium Compound (wt. %) | Corn Starch (wt. %) | Phosphoric acid (wt. %) |
|---|---|---|---|---|---|---|
| SO-15A | sucrose | 98 | carbonate | 2 | | |
| AMS-93 | HFCS | 56.3 | carbonate | 19.1 | | 22.5 |
| AMS-177 | dextrose | 14.7 | phosphate | 19.4 | 22 | 43.9 |
| AMS-180 | dextrose | 14.7 | urea | 19.4 | 22 | 43.9 |
| AMS-182 | dextrose | 14.7 | melamine | 19.4 | 22 | 43.9 |
| AMS-183 | dextrose | 14.7 | thiourea | 19.4 | 22 | 43.9 |
| AMS-188 | | | phosphate | 19.4 | 36.7 | 43.9 |
| AMS-188 | | | phosphate | 19.4 | 36.7 | 43.9 |
| AMS-189 | | | urea | 19.4 | 36.7 | 43.9 |
| AMS-190 | | | melamine | 19.4 | 36.7 | 43.9 |
| AMS-191 | | | sulfate | 19.4 | 36.7 | 43.9 |
| AMS-192 | | | thiourea | 19.4 | 36.7 | 43.9 |
| AMS-193 | | | phos/thiourea | 32.6 | 30.7 | 36.7 |
| AMS-194 | | | none | | 45.5 | 54.5 |
| AMS-195 | | | phosphate | 21.8 | 28.8 | 49.3 |
| AMS-196 | | | phosphate | 26.8 | 33.3 | 39.9 |
| AMS-197 | | | none | | 59.5 | 40.5 |
| AMS-198 | | | phos/thiourea | 19.6 | 36.6 | 43.8 |
| AMS-199 | | | phosphate | 30 | 25 | 44 |
| AMS-202 | | | phosphate | 9.1 | 40.9 | 50 |
| AMS-205 | sucrose | 36.7 | phosphate | 19.4 | | 43.9 |
| AMS-206 | dextrose | 36.7 | phosphate | 19.4 | | 43.9 |
| AMS-207 | fructose | 36.7 | phosphate | 19.4 | | 43.9 |

Table 2 summarizes quantitative elemental analyses of the carbons of the present invention. We were able to prepare carbons with nitrogen contents ranging from 0 to 10% using all of the nitrogen containing compounds. In contrast, we found that ammonium sulfate left very little sulfur in the resulting carbon, while thiourea was effective in increasing the sulfur content to almost 5%.

TABLE 2

Elemental Analysis of Carbon Sorbents

| Sample ID | C (wt. %) | H (wt. %) | N (wt. %) | O (wt. %) | S (wt. %) | Ash (wt. %) |
|---|---|---|---|---|---|---|
| SO-15A | 97.84 | 0.67 | 0.1 | 0.6 | | 0.39 |
| AMS-93 | 82.55 | 0.57 | 2.64 | 7.7 | | |
| AMS-177 | 77.06 | 1.81 | 7.14 | 10.34 | | 0.51 |
| AMS-188 | 77.9 | 1.76 | 6.05 | 10.67 | | <1 |
| AMS-189 | 67.72 | 1.86 | 8.58 | 15.9 | | 1 |
| AMS-190 | 71.91 | 1.64 | 9.73 | 12.38 | | <1 |
| AMS-191 | 76.24 | 1.64 | 7.03 | 11.35 | 0.11 | 1 |
| AMS-192 | 68.81 | 1.61 | 8.35 | 12.28 | 4.69 | <1 |
| AMS-194 | 83.98 | 2.08 | 0.26 | 9.76 | | 0.54 |
| AMS-195 | 72.3 | 2.03 | 5.9 | 14.45 | | 0.33 |
| AMS-196 | 71.14 | 1.98 | 6.66 | 14.56 | | 0.41 |
| AMS-197 | 83.31 | 1.96 | 0.29 | 10.28 | 0.01 | 2.06 |
| AMS-198 | 71.07 | 1.97 | 6.92 | 13.62 | 2.06 | 0.84 |
| AMS-199 | 68.78 | 1.93 | 7.06 | 16.33 | | 0.9 |
| AMS-202 | 76.88 | 1.87 | 3.01 | 12.05 | 0.04 | 0.33 |
| AMS-205 | 80.49 | 1.95 | 4.9 | 8.55 | | 0.61 |

Table 3 summarizes surface area and pore-size measurements by Brunauer-Emmett-Teller (BET) and Density Functional Theory (DFT) analysis using a Micrometrics instrument using nitrogen as the adsorbate. We can tune the mesopore volume from 0 to 0.55 cc/g. As shown in Table 3, we can adjust the mesopore size from 2 to 50 nm by adjusting the carbon precursor formulations.

TABLE 6

BET Surface Areas and DFT Pore Volumes of Carbon Sorbents

| ID | BET Surface Area (m²/g) | DFT TPV < 63 nm (cc/g) | DFT Pore Vol. 2-50 nm (cc/g) | DFT Micropore Vol. < 2 nm (cc/g) |
|---|---|---|---|---|
| AMS-177 | 1021 | 0.49 | 0.15 | 0.33 |
| AMS-180 | 605 | 0.26 | 0.025 | 0.23 |
| AMS-182 | 1028 | 0.44 | 0.049 | 0.4 |
| AMS-183 | 722 | 0.3 | 0.0083 | 0.29 |
| AMS-188 | 1105 | 0.93 | 0.53 | 0.36 |
| AMS-189 | 651 | 0.28 | 0.027 | 0.25 |
| AMS-190 | 893 | 0.4 | 0.071 | 0.33 |
| AMS-191 | 1016 | 0.44 | 0.049 | 0.39 |
| AMS-192 | 631 | 0.26 | 0.0093 | 0.25 |
| AMS-193 | 401 | 0.17 | 0.008 | 0.17 |
| AMS-194 | 1338 | 0.72 | 0.38 | 0.34 |
| AMS-195 | 1163 | 0.89 | 0.45 | 0.4 |
| AMS-196 | 272 | 0.32 | 0.28 | 0.037 |
| AMS-197 | 889 | 0.37 | 0.1 | 0.27 |
| AMS-198 | 1112 | 0.64 | 0.16 | 0.46 |
| AMS-199 | 1667 | 1.06 | 0.55 | 0.51 |
| AMS-202 | 884 | 0.55 | 0.19 | 0.27 |
| AMS-203 | 1320 | 0.65 | 0.22 | 0.44 |
| AMS-205 | 718 | 0.35 | 0.044 | 0.29 |
| AMS-206 | 903 | 0.74 | 0.13 | 0.31 |
| AMS-207 | 632 | 0.28 | 0.01 | 0.27 |
| AMS-212 | 1221 | 0.54 | 0.0061 | 0.53 |

Figure 3:
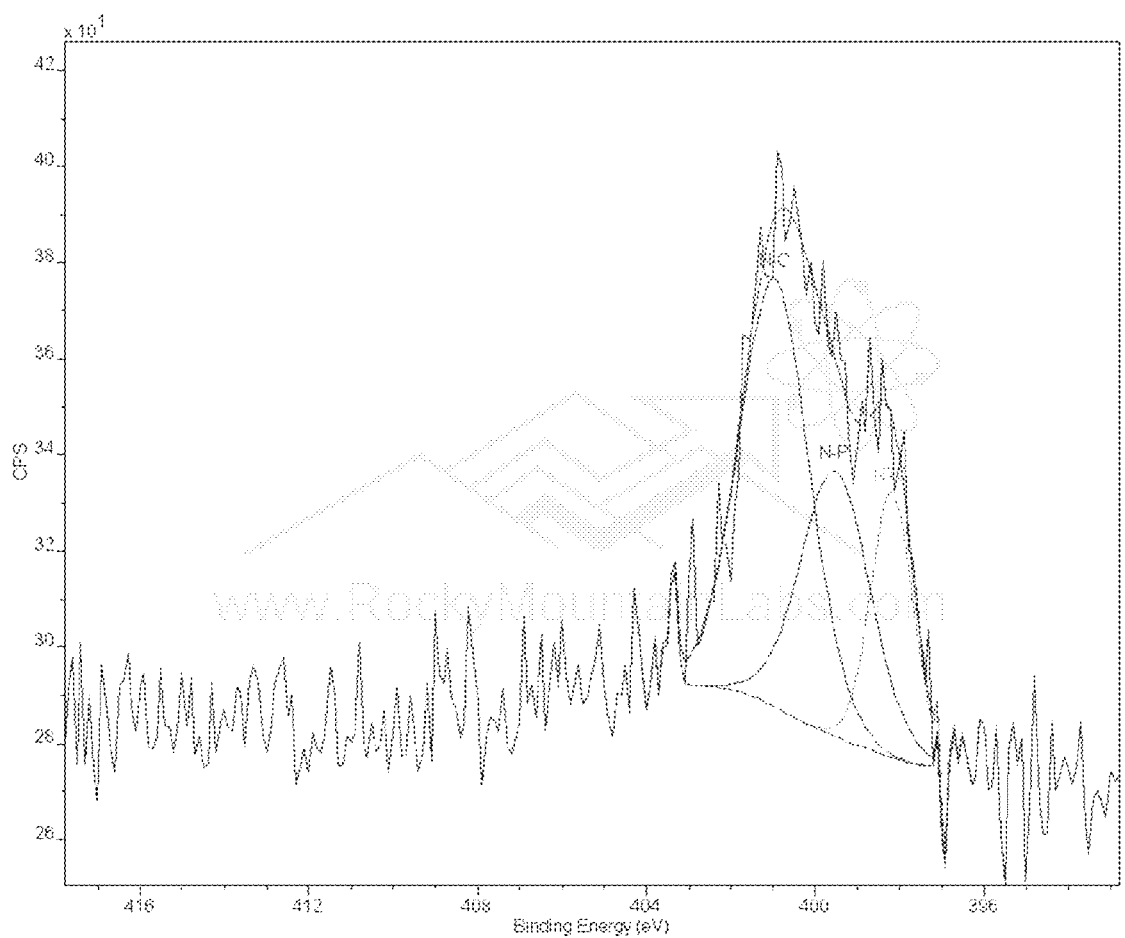
FIG. 3. High resolution XPS spectrum of the N 1s region of sample AMS-188.

High-Resolution XPS Analysis-Nitrogen. X-ray photoelectron spectroscopy was performed on carbons using an Al Kα (1486.3 eV) radiation source. Carbons rich in N such as AMS-93, AMS-177, AMS-188 and AMS-202 exhibited similar features in the N 1s region. FIG. 3 shows a high-resolution XPS of the N 1s region of AMS-188. The deconvoluted peak at 398.2 eV, accounting for 18.7 atom % of the nitrogen, is assigned to pyridine-like nitrogen at carbon edge sites. A second deconvoluted peak at 401.0 eV occurs at the binding energy of both pyrrolic and pyridonic nitrogen. Therefore, the deconvoluted peak at 401.0 eV, accounting for 50.1% of the nitrogen in Sample AMS-188 is assigned to pyridone/pyrrole at carbon edge sites. A third deconvoluted peak at 399.5 eV is assigned to N—P bonds, accounting for 31.1 atom % of the nitrogen in sample AMS-188.

In the carbons of the present invention, the conventional functional groups are largely replaced by nitrogen groups incorporated into graphitic edge sites as pyridinic, pyridonic/pyrrolic and N—P species. Additional edge sites are occupied by cross-linking agents of phosphates, polyphosphates and phosphonates. Chemical binding of the Pt-group metals to N and the various phosphorus species augments trapping of bulky metal species within pores, which is the principle mechanism of metal capture. The preferred formulations react cornstarch and/or glucose with $H_3PO_4$ in the presence of $(NH_4)_2HPO_4$. In aqueous solutions, phosphoric acid acid-hydrolyzes starch into its glucose monomers (or into short-chain carbohydrates). AMS-188 contains 4.6 atom % total nitrogen as measured by XPS.

Figure 4:
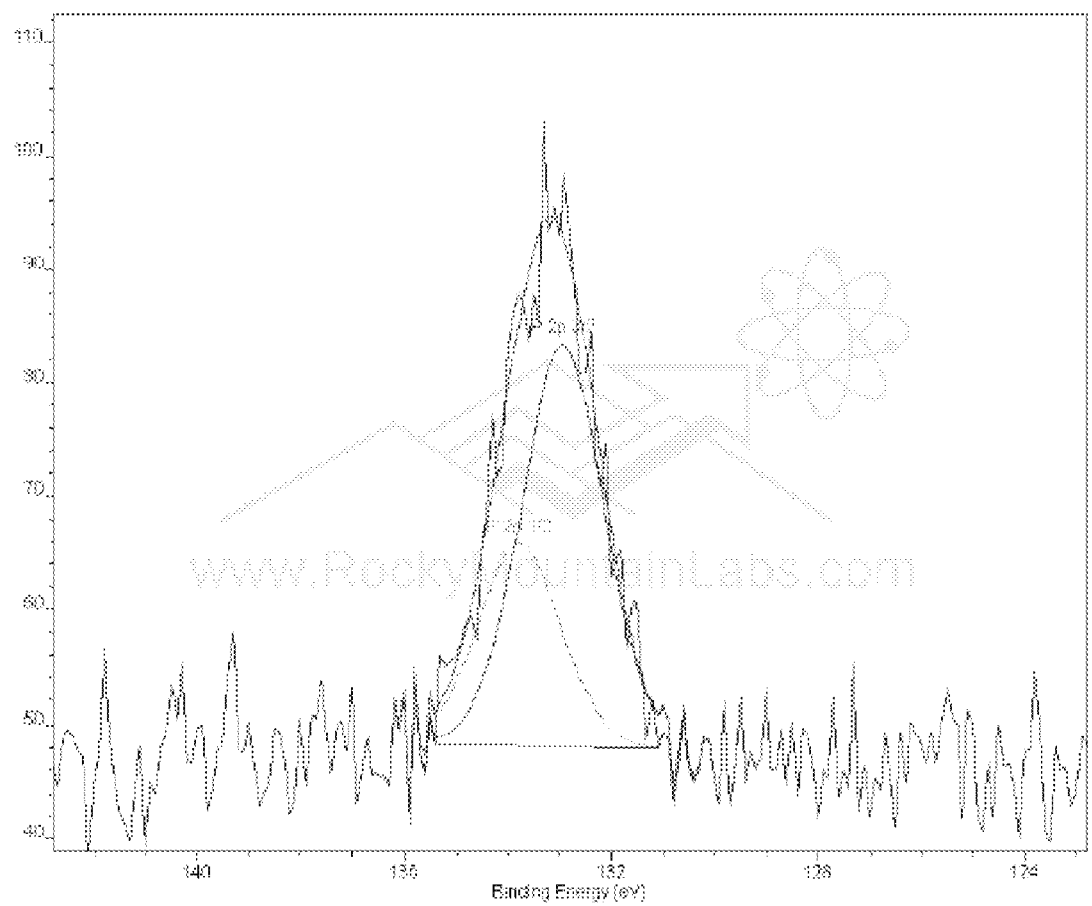
FIG. 4. High resolution XPS spectrum of the P 2p region of sample AMS-188.

XPS Analysis-Phosphorus. FIG. 4 shows high-resolution XPS signals from $P\ 2p_{3/2}$ and $P\ 2p_{1/2}$ orbitals of sample AMS 188. The binding energy is consistent with phosphorus bound to an electronegative element (P—O, P—N and P=N bonds). Upon heating to 500-600° C. there is a ~1 eV shift from 133.7-133.9 eV to 132.7-132.9 eV, the latter which is assigned to phosphonates containing C—P bonds. This shift is seen in samples heated to 535° C. (Samples, AMS-93 and AMS-188). Elemental composition by combustion give an atomic ratio of P:O of near 1:4, which is consistent with the stoichiometry of residual phosphate, $PO_4^{3-}$. Sample AMS-188 produced a pH of 2.4 consistent with phosphorous-based and chemically bound acid sites. The observed acidity is consistent with the presence of a P—O—H unit in a polyphosphate, which is not removed by washing in water and which is not neutralized by NaOH or KOH as in conventional carbons. Infrared and XPS analysis indicate only few carboxylic acid groups, which, therefore, are not responsible for the acidic pH, making polyphosphoric acid $(HPO_3)_n$, the groups producing the acidic pH. Sample AMS-188 contained 1.8 atom % total phosphorous as measured by XPS.

Figure 5:
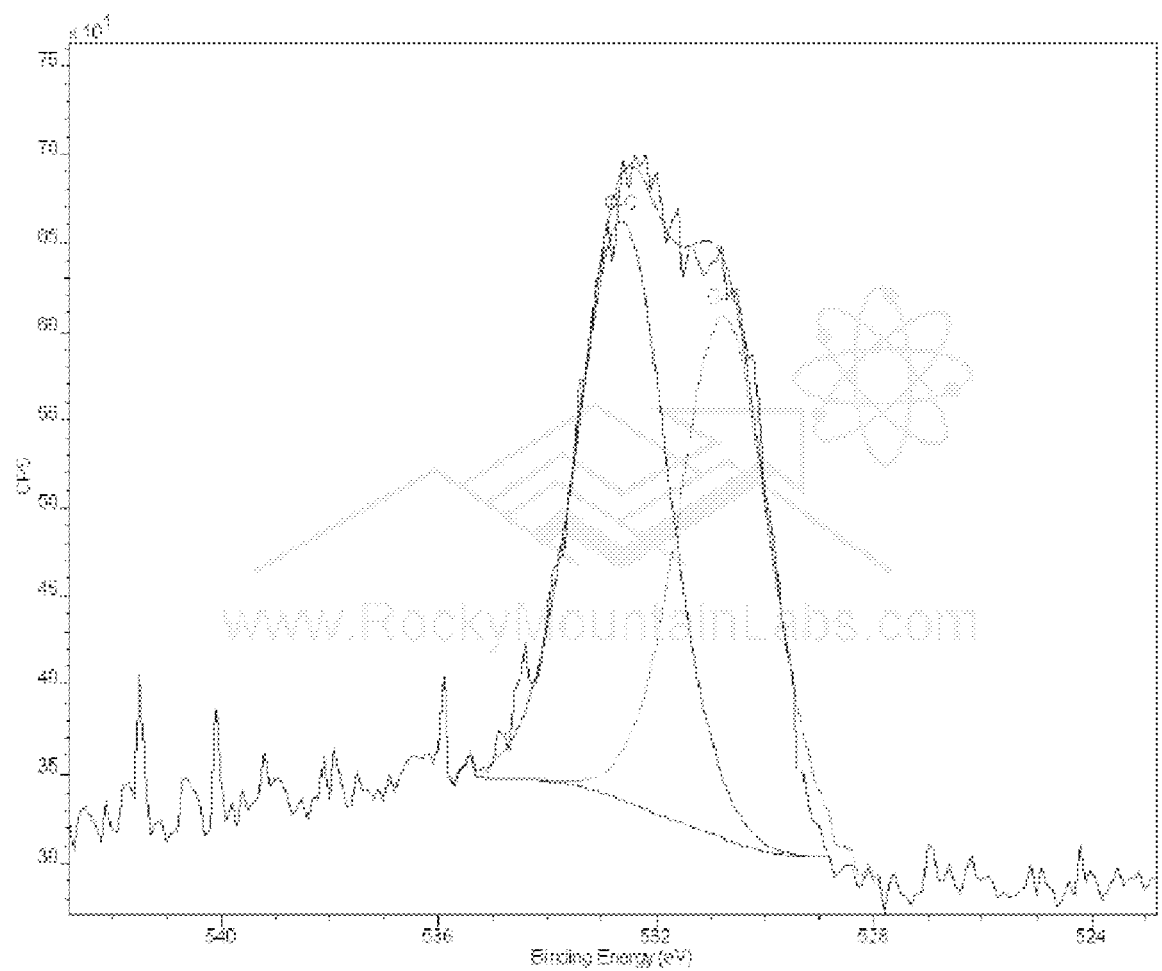
FIG. 5. High resolution XPS spectrum of the O 1s region of sample AMS-188.

XPS of Oxygen. FIG. 5 shows high-resolution XPS of the O 1s region and indicates two chemical types of oxygen. The spectrum is consistent with presence of a polyphosphate along with C—OH hydroxyl groups. Samples were degassed in vacuum to remove weakly-bound water and other vapors by pumping at room temperature overnight to yield a base pressure in a cryo-cooled sample chamber of below $1\times10^{-10}$ torr. Water was desorbed and was not present in any significant amount as indicated by the XPS of the oxygen 1s region, which showed negligible electron emission at both 536.4 eV, expected for physically adsorbed water, and at 535.0 eV, expected for non-dissociated chemisorbed water. AMS-188 contains 9.9 atom % total oxygen as measured by XPS.

Figure 6:
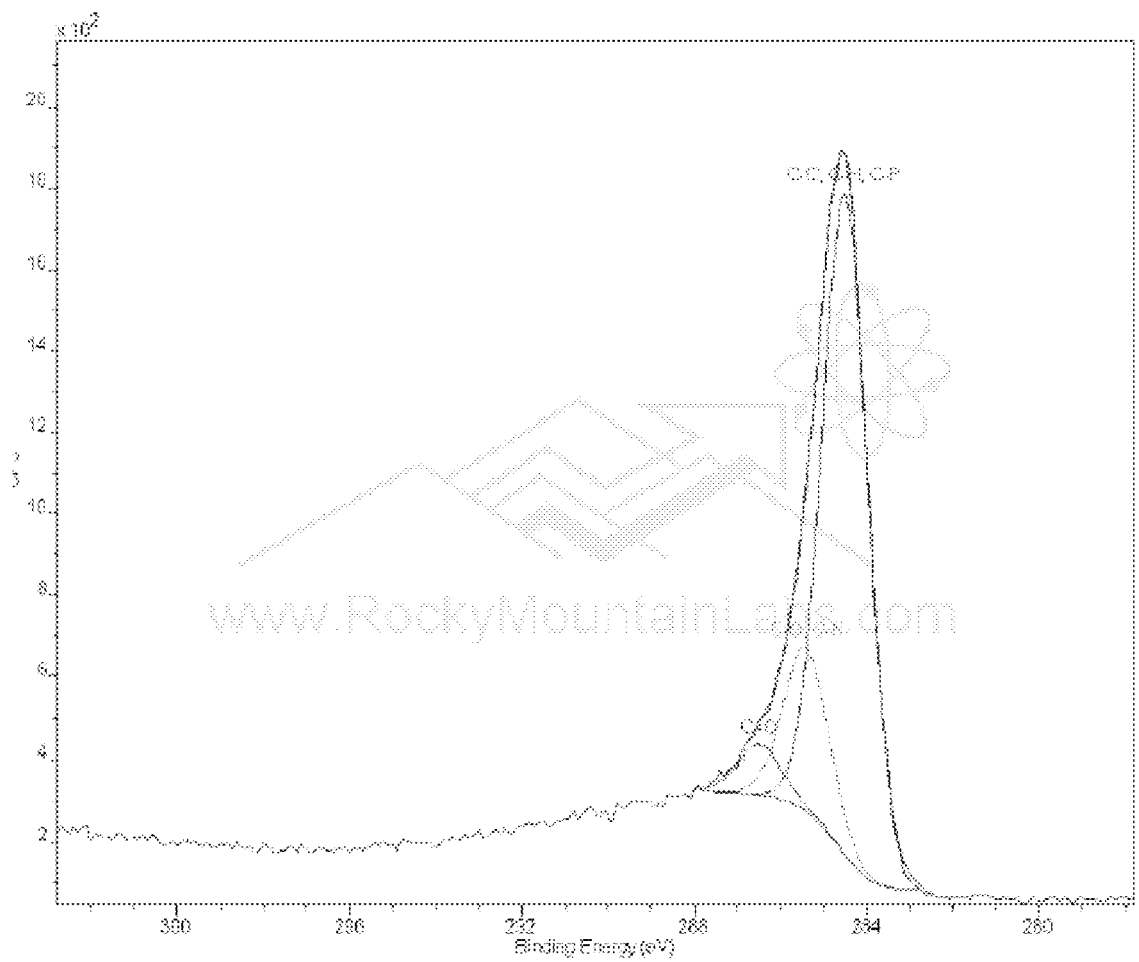
FIG. 6. High resolution XPS spectrum of the C 1s region of sample AMS-188.

High-Resolution XPS—Carbon. Observed at 284.5 eV in FIG. 6 is the C 1s peak for graphitic carbon, 75.8% of the carbon in Sample AMS-188 is assigned to $sp^2$-hybridized carbon in graphitic basal planes. The considerable remaining 24.2% of non-graphitic carbon in the de-convoluted peaks with higher binding energy is assigned to C bound to more electronegative N and O, most at carbon-edge sites. The carbons of the present invention that are heated to just above 500° C. contain direct C—P bonds as indicated by XPS shift of the P 2p peaks and their vibrations seen by FTIR. Samples richer in nitrogen show higher intensity of the C 1s peak at 285.6 eV, in accord with assignment of C bound to N. The C 1 s peak at 286.5 eV was assigned to C atoms bound to both N and O as in pyridone and its lactam tautomers, the latter having C=O bonds (5.6 atom % for carbon in AMS-188). The deconvoluted peak at 285.4 eV is assigned to C—O and C—N groups accounting for 18.6 atom % for the carbon in AMS-188.

Summary of X-ray Photoelectron Spectroscopy to determine the elemental composition on the surface of the carbons, the carbons were analyzed by XPS. The major elements that could be detected were carbon, nitrogen, oxygen and phosphorus (Table 4). In Table 4 there are two carbons SO-15A and AMS-93 that are described in the next paragraphs. The other carbons were described above.

Preparation of SO-15A. Combined 2% ammonium bicarbonate, 1% canola oil and 98 wt. % sucrose. The components were thoroughly mixed in a standard Kitchen Aid mixer. The mixture was added to Teflon trays and heated to 220° C. for 2 hours in a Despatch box oven. The char was removed and ground with a Bico Chipmunk jaw crusher. The crushed material was screened in a Sweco sifter and the −4 to +20 mesh cut was collected. The granular char was carbonized at 950° C. under nitrogen for 2 hours and activated with carbon dioxide at 950° C. in a rotary kiln for 20 hours. The product was ball-milled and screened to −325 mesh (BET surface area 1517 $m^2/g$).

AMS-93 was prepared as follows: 19.1 wt. % ammonium carbonate, 56.3 wt. % 55% high fructose corn syrup and 22.5 wt. % phosphoric acid (85%) were thoroughly mixed in a standard Kitchen Aid mixer. The mixture is poured into Teflon pans and heated in the convection oven at 220° C. to drive off the water and decompose the carbohydrate to give a black char. The char was removed from the Teflon tray and broken up into 4×20 mesh size particles. The particles were loaded into Inconel trays and heated to 535° C. under flowing nitrogen to be carbonized. The carbon was then washed with distilled water using a Soxhlet extractor to remove the phosphoric acid and then dried at 110° C. for 24 hours (BET surface area 732 $m^2/g$).

TABLE 4

Relative elemental composition of sample surfaces as determined by XPS.

| Carbon Sample | C (Atom %) | N (Atom %) | O (Atom %) | P (Atom %) |
|---|---|---|---|---|
| SO-15A | 97 | ND | 3.5 | ND |
| AMS-93 | 84 | 4.8 | 9.3 | 1.8 |
| AMS-177 | 84 | 6.7 | 8.6 | 1.1 |
| AMS-188 | 84 | 4.6 | 9.9 | 1.8 |
| AMS-202 | 88 | 3.4 | 7.4 | 0.8 |

TABLE 5

Relative compositions and most probable peak assignments for carbon species on sample surfaces as determined by XPS, C 1s region.

| Carbon Sample | C—C, C—H, C—P (Atom %) | C—O, C—N (Atom %) | C=O (Atom %) |
|---|---|---|---|
| SO-15A | 83 | 13 | 5.0 |
| AMS-93 | 77 | 17 | 6.0 |
| AMS-177 | 62 | 29 | 8.9 |
| AMS-188 | 76 | 19 | 5.6 |
| AMS-202 | 76 | 17 | 7.1 |

TABLE 6

Relative compositions and most probable peak assignments for oxygen species on sample surfaces as determined by XPS, O 1s region.

| Carbon Sample | O—C (Atom %) 93 | O=C (Atom %) |
|---|---|---|
| SO-15A | 54 | 46 |
| AMS-93 | 54 | 46 |
| AMS-177 | 50 | 50 |
| AMS-188 | 53 | 47 |
| AMS-202 | 58 | 42 |

Aside from AMS-202 the samples showed no oxidized nitrogen. The reason that oxidized nitrogen was detected with this sample is because less diammonium phosphate was included in the initial formulation. The peak energies suggest that the carbons have a mixture of nitrogen in the form of pyridine and pyridone/pyrrole-like groups. Half or more of the nitrogen is in the form of pyridine-like groups. It is not possible to distinguish between pyridone and pyrrole by XPS. In addition, some samples have N—P bonding as well. The samples without N—P bonds were processed at lower temperatures (less than 535° C.).

TABLE 7

Relative compositions and most probable peak assignments for nitrogen species on sample surfaces as determined by XPS, N 1s region.

| Carbon Sample | N—C pyridine (Atom %) | N—C pyridone/pyrrole (Atom %) | N—P | N—O |
|---|---|---|---|---|
| SO-15A | ND | ND | ND | ND |
| AMS-93 | 30 | 71 | ND | ND |
| AMS-177 | 23 | 56 | 21 | ND |
| AMS-188 | 19 | 50 | 31 | ND |
| AMS-202 | 14 | 50 | 24 | 12 |

Potential impurities, and especially Na and K seen in high concentrations in many commercial carbons produced from wood with KOH or NaOH neutralization, do not rise above the noise level in XPS, implying surface concentrations of less than 0.1 atom % of these elements in the carbons of the present invention.

The above example (AMS-188) is consistent with other similar formulations using cornstarch (and/or cornstarch with sugar), $H_3PO_4$ and $(NH_4)_2HPO_4$.

pH of sorbents: The pH of the carbon sorbents were measured according to ASTM D 1512-95 (Standard Test Methods for Carbon Black-pH Value, Reapproved 2000). Using the Soxhlet Extraction Method for a duration of 24 hours, AMS-188 was found to have pH=2.4. Using the Filter Press Method with 3 washes, AMS-188 was found to have pH=6.0.

Sorbent testing: To evaluate the ability of the carbon sorbents to capture metals from reaction mixtures, we tested the carbons against the product mixture of a the Suzuki coupling reaction with a palladium complex catalyst, a Stille coupling reaction with a palladium complex and also a tin co-reactant, and lastly, a metathesis reaction involving Grubbs catalyst, which was the source of ruthenium.

To test the efficiency of the carbons for palladium removal, we carried out a Suzuki coupling reaction, scheme 1, and then purified the reaction products. The product of the reaction was extracted with toluene and 20% NaHSO$_3$ to reduce the Pd content to ~200 ppm in dried product. The Pd sample test extraction procedure was to add 0.15 g sorbent to 0.3 g Active Pharmaceutical Ingredient "API", a 0.5 to 1.0 ratio, dissolved in 10 mL of acetonitrile ([Pd]=1.3 ppm). The mixture was stirred overnight at room temperature and filtered through a 0.45-micron syringe filter and dried. Samples were analyzed by ICP-MS analysis. The results are shown in Table 7. The carbons with high mesopore volumes removed more Pd than other carbons.

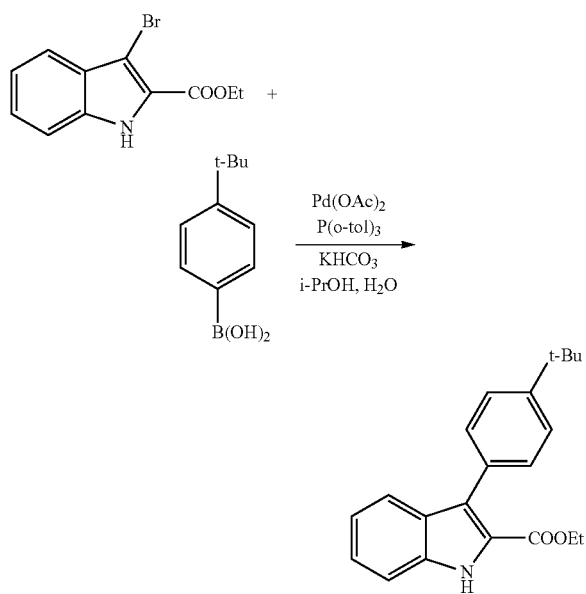

Scheme 1 (Suzuki coupling reaction)

TABLE 7

Palladium removal from Suzuki coupling reaction product mixture.

| Sample | Pd Removal % (ratio 0.5:1 grams sorbent to grams API) | DFT Mesopore Vol. 2-50 nm (cc/g) | pH (ASTM method) |
| --- | --- | --- | --- |
| TDA-177 | 96 | 0.15 | 3.1 |
| TDA-180 | 41 | 0.025 | |
| TDA-182 | 73 | 0.049 | |
| TDA-183 | 39 | 0.0083 | |
| TDA-188 | 96 | 0.53 | 2.0 |
| TDA-189 | 69 | 0.027 | |
| TDA-190 | 70 | 0.071 | |
| TDA-191 | 83 | 0.049 | |
| TDA-192 | 31 | 0.0093 | |
| TDA-194 | 90 | 0.38 | 2.7 |
| TDA-195 | 94 | 0.45 | 2.4 |
| TDA-202 | 97 | 0.45 | 3.2 |
| TDA-203 | 97 | 0.01 | 3.1 |
| TDA-205 | 85 | 0.044 | 2.4 |

TABLE 7-continued

Palladium removal from Suzuki coupling reaction product mixture.

| Sample | Pd Removal % (ratio 0.5:1 grams sorbent to grams API) | DFT Mesopore Vol. 2-50 nm (cc/g) | pH (ASTM method) |
| --- | --- | --- | --- |
| TDA-206 | 93 | 0.13 | |
| TDA-212 | 42 | 0.0061 | 3.1 |

Figure 7:
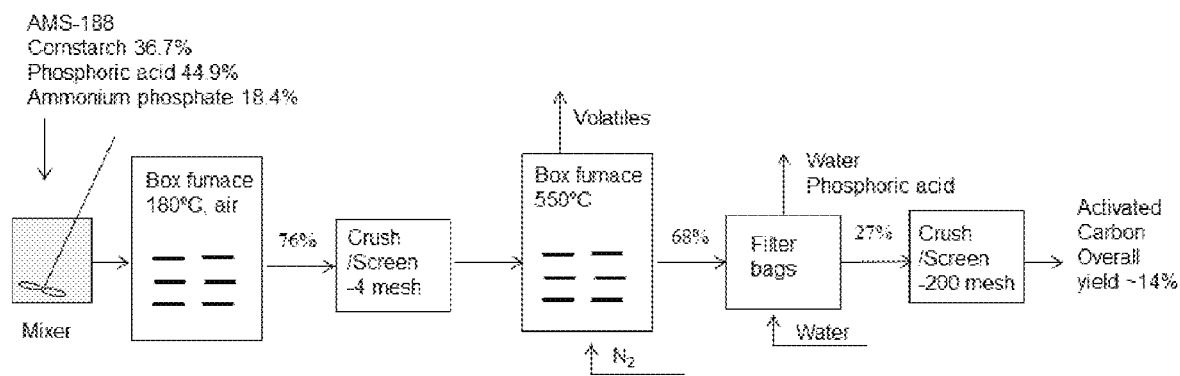
FIG. 7. Method of producing the carbon sorbents.

General preparation method for carbon sorbents: FIG. 7 shows the process flow diagram for producing the carbon sorbent of the present invention. The diagram is representative of sample AMS-188, but the same method applies to the other formulations in Table 1. The first step was to mix the ingredients, which include the carbon precursor (cornstarch, sucrose and/or dextrose), H$_3$PO$_4$, and ammonium phosphate. The components were mixed using our 20 liter Hobart mixer. The mixture was poured into Teflon pans and heated in the Despatch convection oven at 180° C. to drive off the water and decompose the carbohydrate to give a black char.

The char was removed from the Teflon tray and broken up into 4×20 mesh size particles. These particles were then loaded into Inconel trays and heated to 535° C. under flowing nitrogen to be carbonized. To expand the oven capacity, we installed a second box furnace with retort that has a 16"×13"×12" interior volume to increase our production capacity to 5 pounds/day).

After trying several methods to wash the carbon to remove excess H$_3$PO$_4$, we found that filter bags with 200 mesh pores gave the best results. The carbon filled bag was placed in a breaker of boiling water to dissolve the phosphoric acid. After a few minutes, the bag was removed from the beaker and the water quickly drains from the filter. Using this method, we can wash several hundred grams of carbon per bag in just a few hours. The desired particle size distribution for the final product is 200×400 mesh and it was screened using our Sweco sifter.

Figure 8:
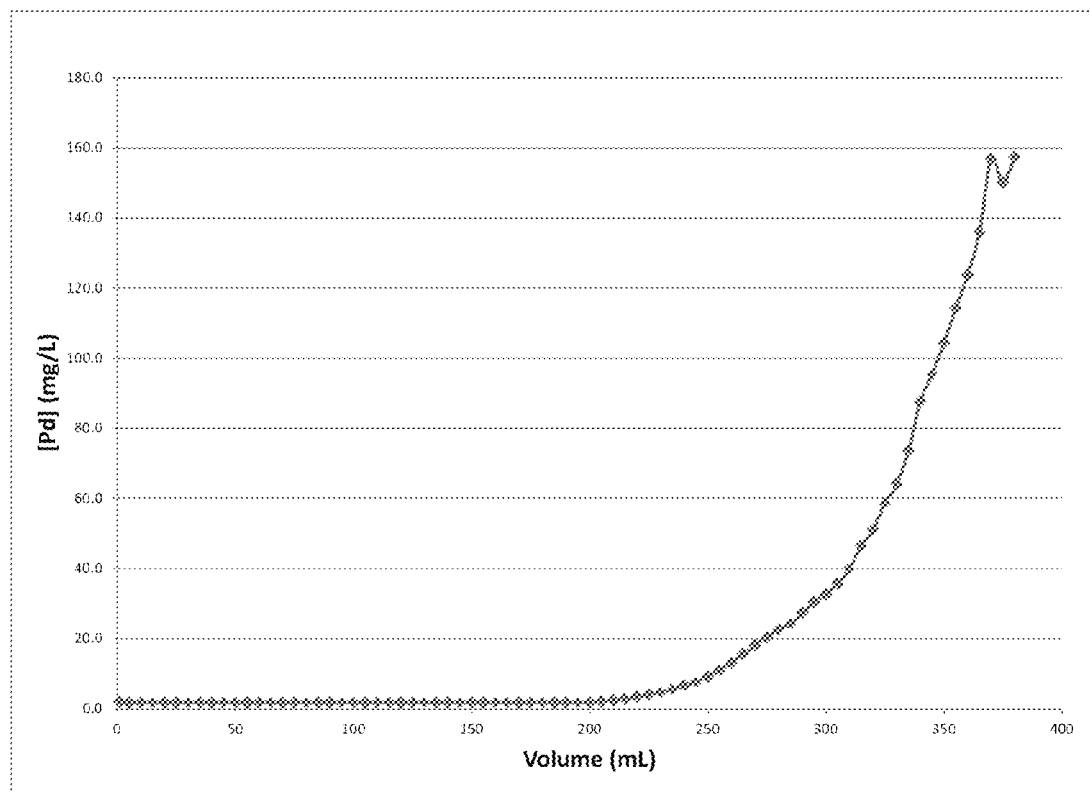
FIG. 8. Pd removal in Pd(OAc)$_2$/THF using carbon sample AMS-188 (12×20 mesh).
Figure 9:
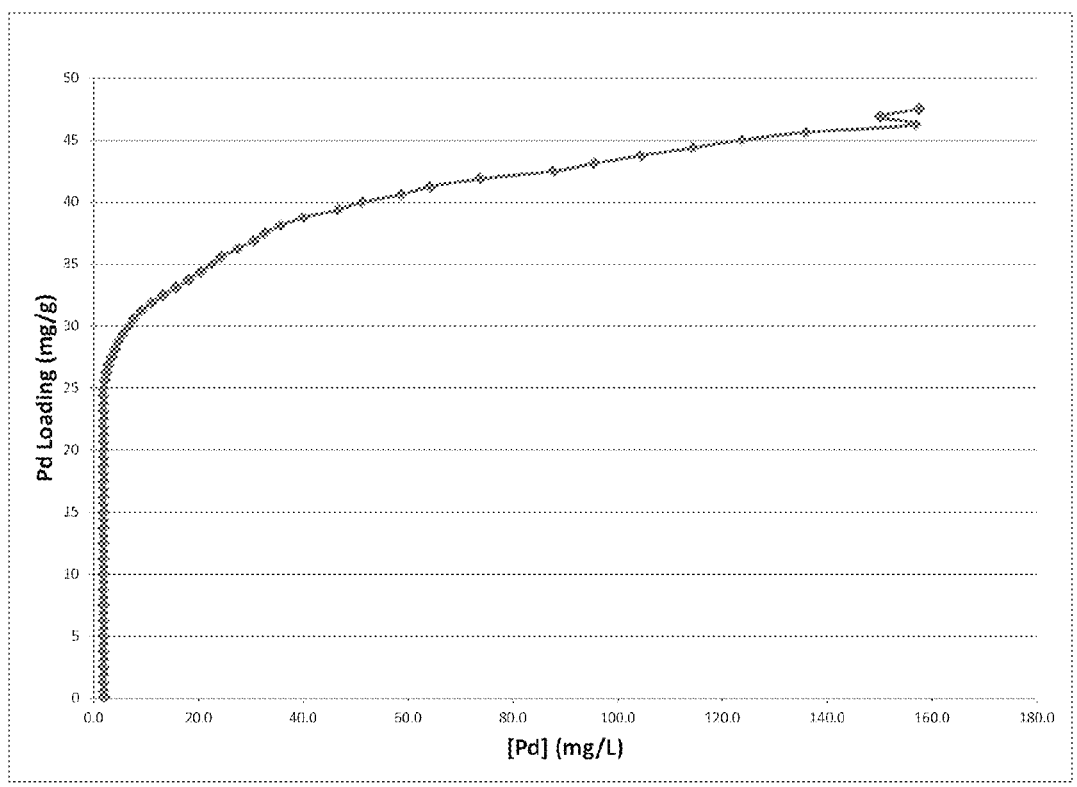
FIG. 9. Pd uptake in Pd(OAc)$_2$/THF using carbon sample AMS-188 (12×20 mesh).

Using carbon sorbents in packed column tests for the removal of palladium: The carbon was packed into a glass column with a 15 mm inside diameter by 300 mm long. For this test, the carbon was in a granular form with particle sizes in the range of 12×20 mesh. The feed solution contained 1000 ppm Pd in the form of palladium acetate dissolved in tetrahydrofuran (THF). FIG. 8. shows that the outlet concentration of the solution was well below the 5 ppm requirement and that the backpressure was essentially zero. At breakthrough, the Pd concentration gradually increased. FIG. 9 shows the palladium uptake on the sorbent during the test.

Figure 10:
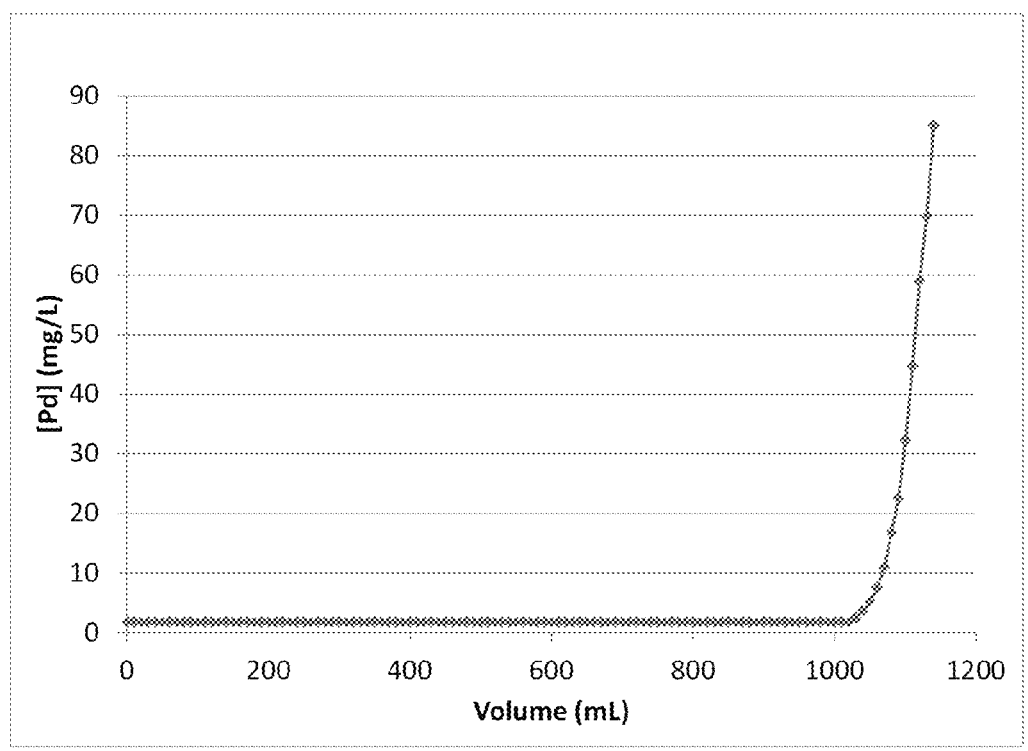
FIG. 10. Removal of [Pd(OAc)$_2$/THF] using carbon sample AMS-188 (less than 200 mesh size).
Figure 11:
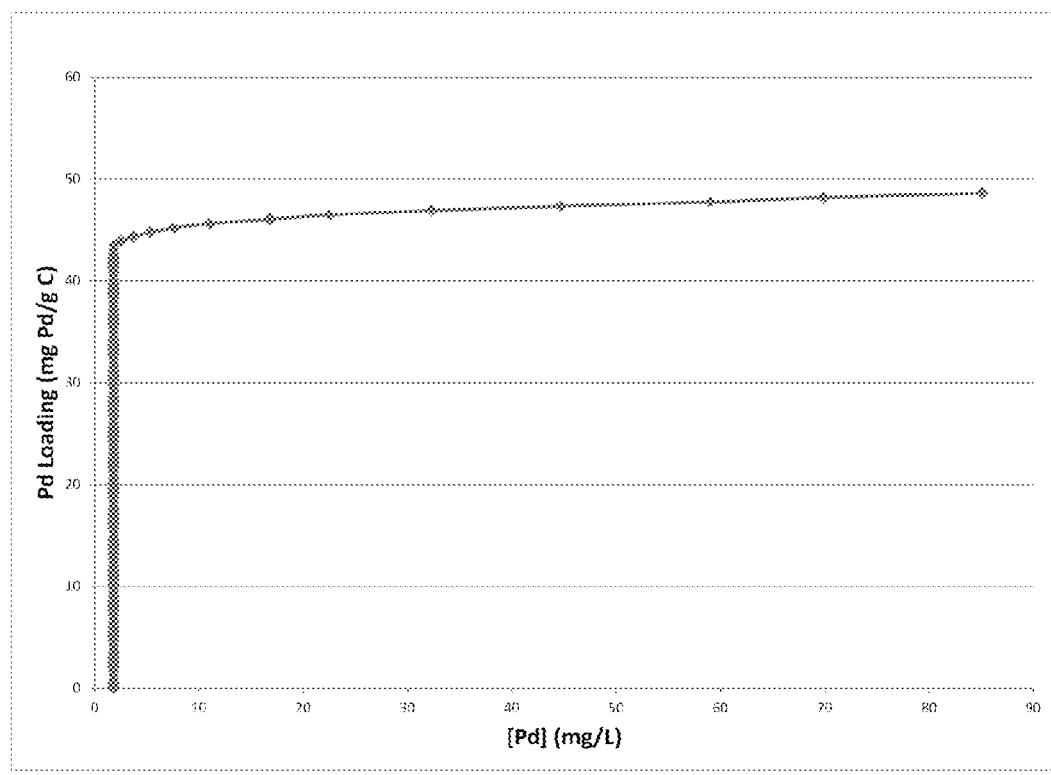
FIG. 11. Pd uptake in Pd(OAc)$_2$/THF using carbon sample AMS-188 (less than 200 mesh size).

We then tested the same carbon (AMS-188) in powder form (<200 mesh). The smaller particles gave a much sharper breakthrough curve (FIG. 10 and FIG. 11) due to improved mass transfer (shorter mass transfer zone length). The smaller particles also allow a greater mass of carbon to be packed into the same volume, which increased the total Pd capacity. The only drawback to using the fine particles is a much larger pressure drop (about 50 psi). While much higher, this pressure drop can be accommodated using a conventional solution pump.

Figure 12:
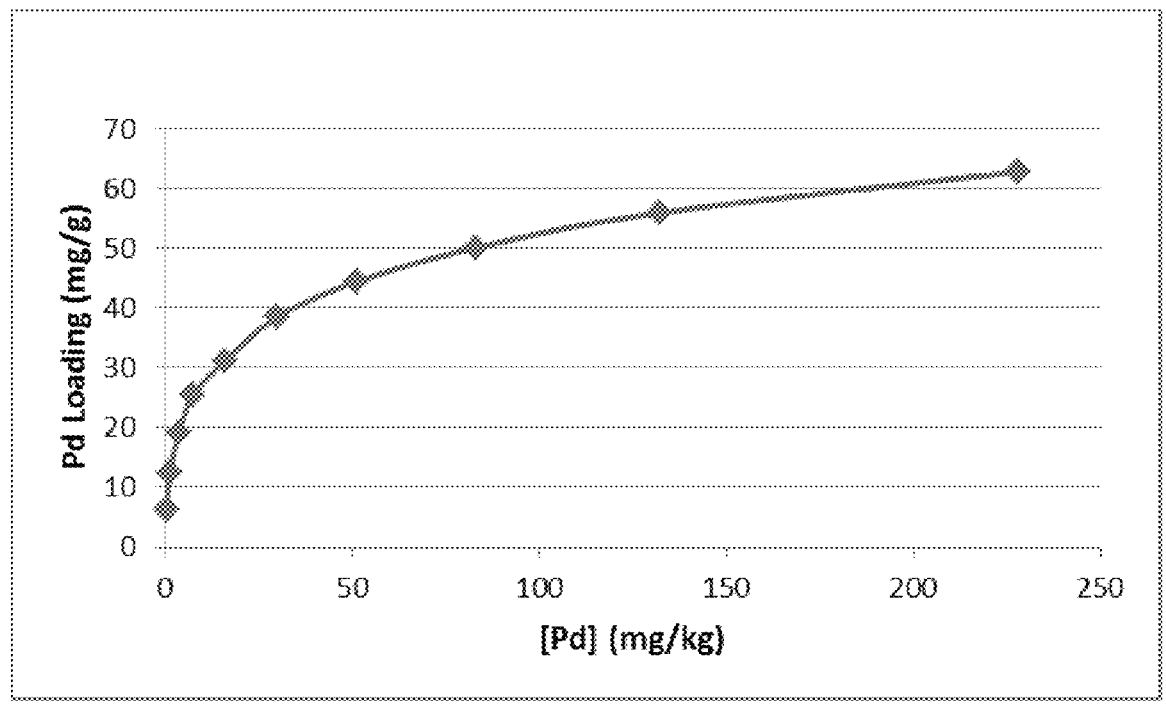
FIG. 12. Pd removal isotherm from acidic water using AMS-188.
Figure 13:
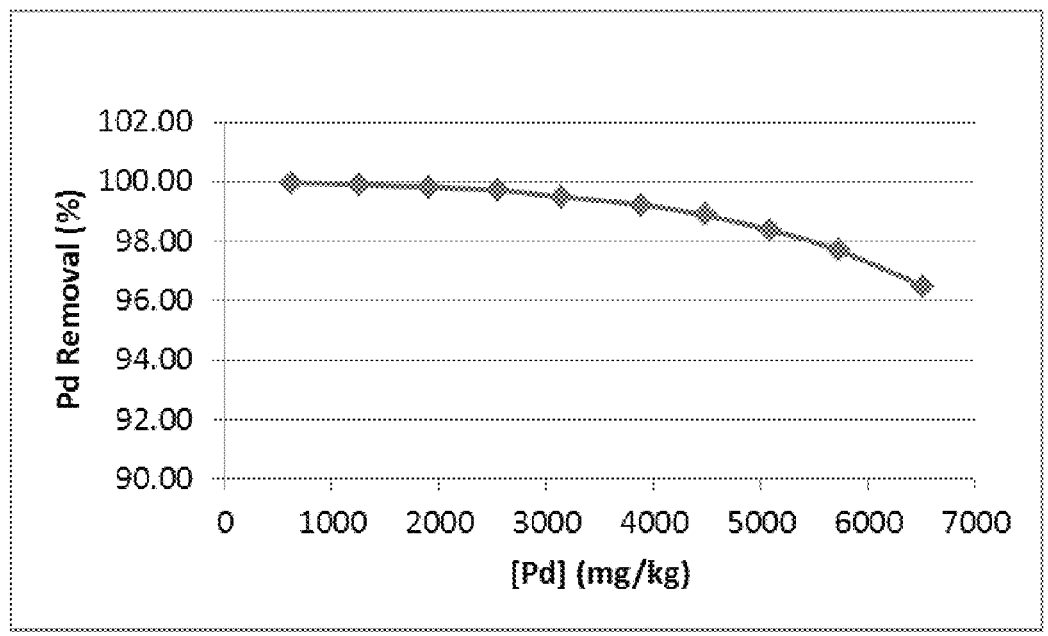
FIG. 13. Pd uptake from acid water using AMS-188.

Pd Removal at Extreme pH. One advantage of the carbon sorbents of the present invention is that they are stable in aqueous solutions at very high and very low pH. This is especially problematic in aqueous solvents at high and low pH's where the silica-based materials that are commonly used in industry for palladium recovery begin to dissolve. To test the carbons of the present invention, palladium chloride was mixed with ammonium chloride in a 1:3 wt. ratio, dissolved in water and the pH adjusted to 0.1 with concentrated HCl. FIG. 12 and FIG. 13 show the equilibrium adsorption isotherms for Pd using AMS-188 carbon in highly acidic aqueous solution (pH=0.1). This carbon exhibits both high capacity and good stability.

Metal removal from model pharmaceutical intermediate compound reaction products: In these examples, carbons of the present invention were used to remove metal catalysts after three reactions commonly used in the pharmaceutical industry. These reactions are commonly used to evaluate all new sorbent materials. The first was Suzuki coupling with a palladium complex, the second was Stille coupling with a palladium complex and also a tin reactant, and the third was a metathesis reaction involving Grubbs catalyst (first generation), which is the source of ruthenium.

Portions of sorbents were placed in pre-weighed 20 mL scintillation vials. Each vial was then filled with a predetermined volume of the solution to be scavenged. The amount of sorbent added to API was a weight ratio of 1.5 to 1. Typical mixtures were 5-15 mL of API solution combined with 15-60 mg of carbon sorbent dependent on the API concentration. The mixtures were shaken for four hours at room temperature and filtered through 1 micron glass microfiber filters. The residual solids were rinsed with a clean portion of the reaction solvent (20% of the initial volume). Filtrates were evaporated. Vials were weighed and the solution was reconstituted with a precise amount of DMF prior ICP-AES injection.

The amount of metal in solution varied for each batch tested in the following ranges: Suzuki coupling: 100-300 mg/L of Pd (150 mL ethyl acetate solution); Stille coupling: 50-300 mg/L of Pd, >3000 mg/L of Sn (80 mL toluene solution); Metathesis reaction: 80-150 mg/L of Ru (170 mL dichloromethane solution).

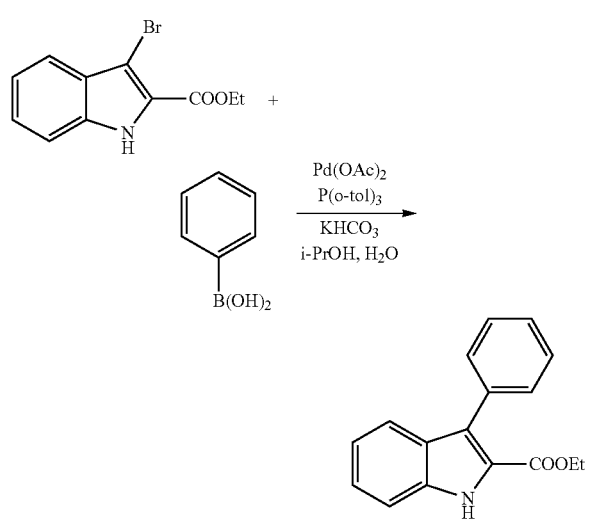

Suzuki coupling is a palladium catalyzed reaction as shown in Scheme 2. The preferred carbons showed Pd scavenging greater than 97% recovery, and preferably at least 99% recovery. Recoveries of API were more variable. AMS-177 had an organic product recovery of 90% (10% adsorbed onto the carbon), AMS-188 had an organic product recovery of 100%, while the AMS-182 sample (with virtually no mesopores) had 0% product recovery (all of it adsorbed on the carbon).

TABLE 8

Results of the model Suzuki reaction #2 tests.

| Sample | % Pd removal | % product recovery | DFT Mesopore Vol. 2-50 nm (cc/g) | BET Surface Area (m²/g) | Total Pore Vol. (cc/g) |
|---|---|---|---|---|---|
| AMS-188 | 97% | 100% | 0.53 | 1030 | 0.56 |
| AMS-177 | 99% | 90% | 0.15 | 1021 | 0.49 |
| AMS-182 | 84% | 0% | 0.049 | 1028 | 0.44 |

Figure 2:
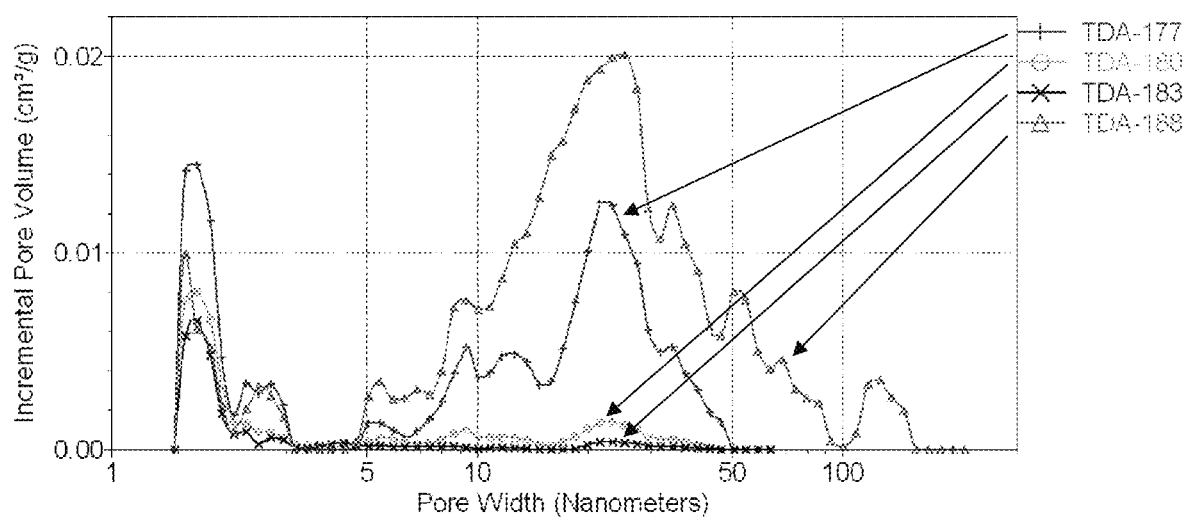
FIG. 2. Incremental pore volume versus pore width (diameter) for representative carbon samples.

The preferred carbons for Palladium removal had large mesopores (preferably with a peak on an incremental pore volume vs. pore diameter plot, see FIG. 2, of greater than 10 nm, and more preferably greater than 20 nm. Although not wishing to be bound by theory, these large mesopores aid liquid diffusion into the pores and the capture of bulky Pd-coordination compounds. Note that AMS-182 and AMS-183 have similar pore size distributions.

Figure 14:
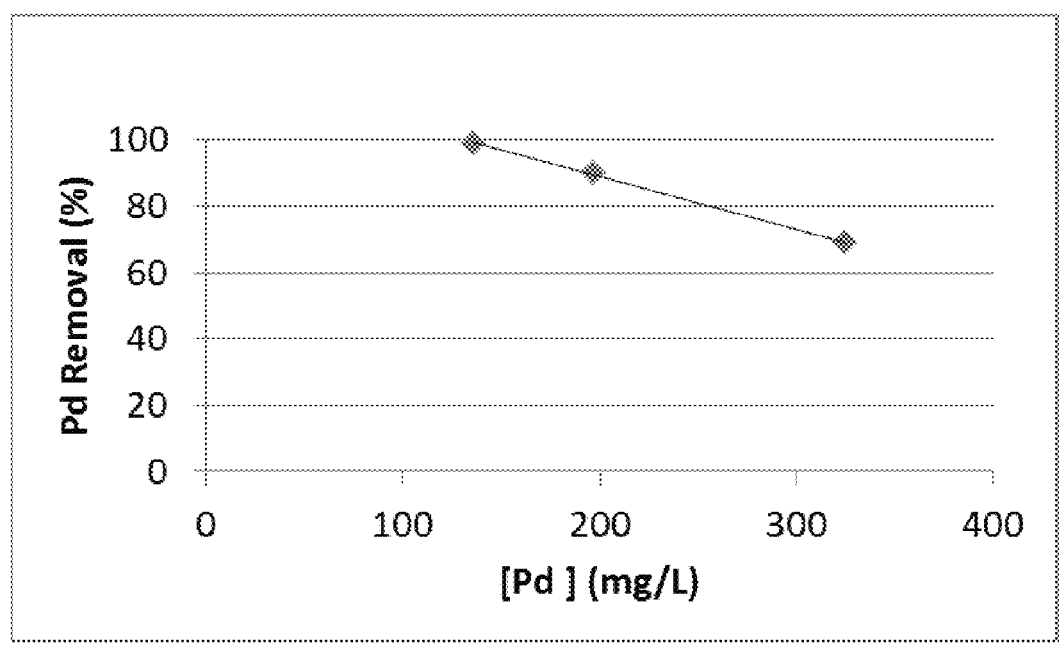
FIG. 14. Percent Pd removal vs. Pd concentration for Suzuki coupling reaction.
Figure 15:
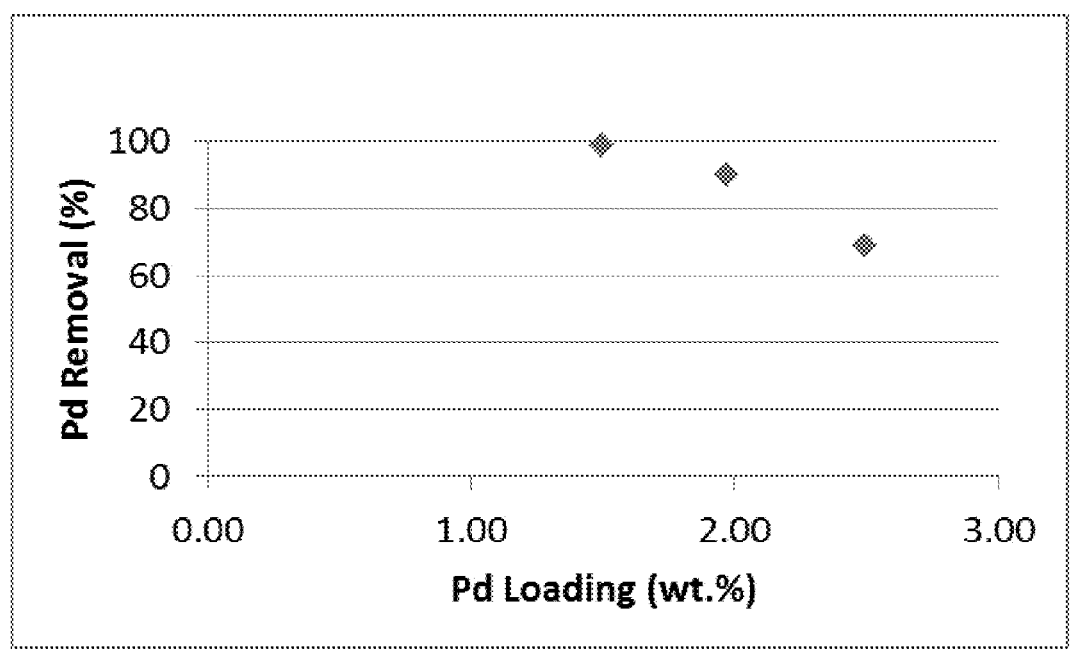
FIG. 15. Percent Pd removal vs. Pd loading for Suzuki coupling reaction.

We found that plotting Pd removal percentage versus Pd concentration for a fixed amount of carbon showed very predictable behavior. For a fixed amount of carbon, the higher the Pd concentration in the solution the lower the % Pd removal (FIG. 14), although the amount of Pd removal per gram of carbon is significantly increased. When we plot the percentage Pd removal versus Pd loading on the carbon (FIG. 15), we found we got 99% Pd removal at 15 mg Pd/g carbon (1.5 wt. % Pd adsorbed on the carbon).

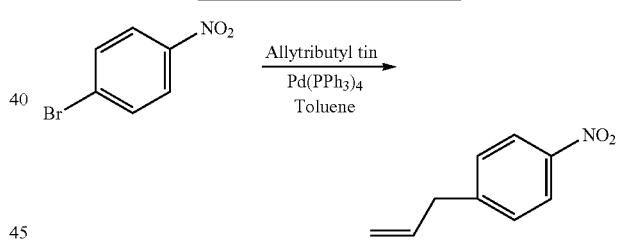

The second screening test was a Stille coupling reaction that uses a Pd catalyst and a tin functionalized reactant (Scheme 3). The carbon sorbents of the present invention were able to remove tin (Table 9). Once again, the carbons with the greatest mesopore volume and pore diameter (preferably having mesopores larger than 10 nm, more preferably larger than 20 nm) showed the highest metals removal percentages for both Pd and Sn.

TABLE 9

Results of the model Stille reaction tests.

| Sample | % Pd removal | % Sn removal | DFT Mesopore Vol. 2-50 nm (cc/g) | BET Surface Area (m²/g) | Total Pore Vol. (cc/g) |
|---|---|---|---|---|---|
| AMS-188 | 67% | 61% | 0.53 | 1030 | 0.56 |
| AMS-177 | 54% | 45% | 0.15 | 1021 | 0.49 |
| AMS-182 | 18% | 15% | 0.049 | 1028 | 0.44 |

Scheme 4 (Metathesis Reaction)

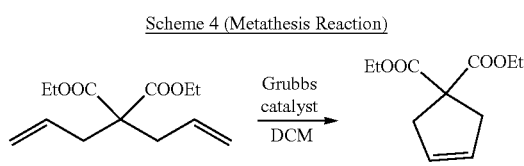 [SMILES: C=CCC(CC=C)(C(=O)OCC)C(=O)OCC ; CCOC(=O)C1(C(=O)OCC)CC=CC1]

The third screening reaction was a metathesis reaction using Grubb's first generation ruthenium catalyst (Scheme 4). We found that the ruthenium removal for preferred carbons was high (greater than 70%) while the product recovery was 100% (no adsorption of the product in the carbon). The carbons with large mesopores captured more metal, whereas the microporous AMS-182 performed very poorly, only adsorbing 1% of the ruthenium. This is consistent with the Suzuki coupling reaction results above that showed that larger mesopores are essential for efficient metal capture.

TABLE 10

Results of the model Grubbs reaction tests

| Sample | % Pd removal | % product recovery | DFT Mesopore Vol. 2-50 nm (cc/g) | BET Surface Area (m²/g) | Total Pore Vol. (cc/g) |
|---|---|---|---|---|---|
| AMS-188 | 73% | 100% | 0.53 | 1030 | 0.56 |
| AMS-177 | 78% | 100% | 0.15 | 1021 | 0.49 |
| AMS-182 | 1% | Not measured | 0.049 | 1028 | 0.44 |

Figure 16:
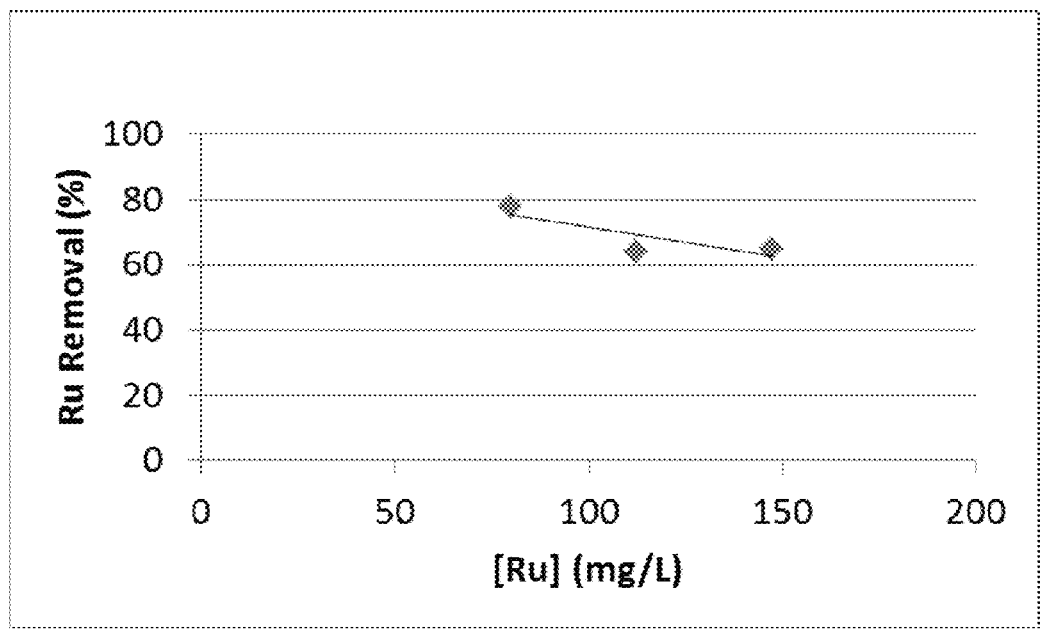
FIG. 16. Percent Ru removal vs. Ru concentration for Metathesis reaction (Grubbs catalyst).
Figure 17:
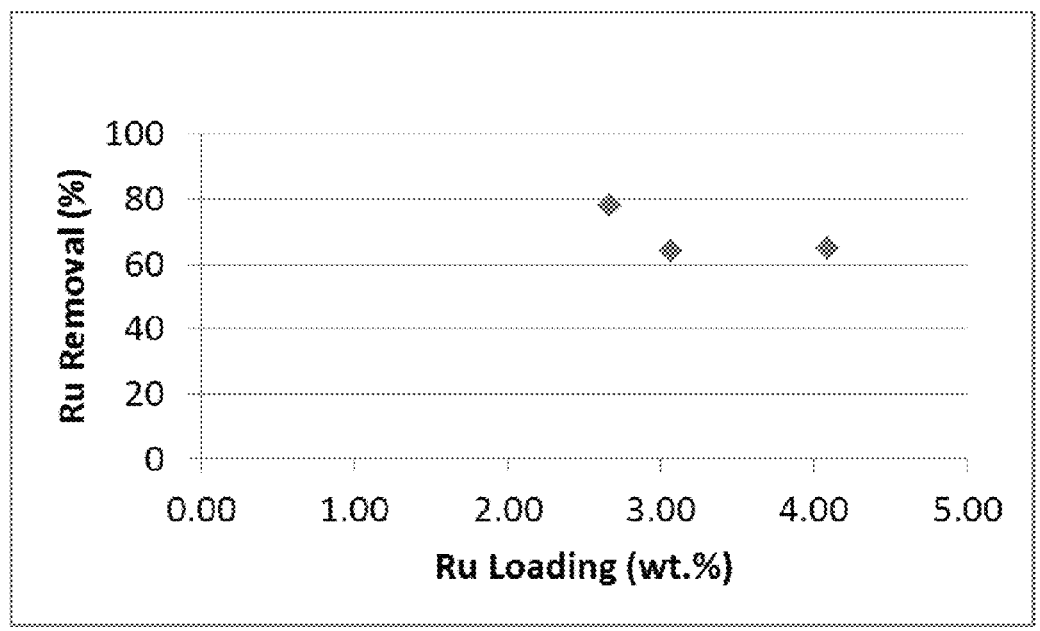
FIG. 17. Percent Ru removal vs. Ru loading for Metathesis reaction (Grubbs catalyst).

FIG. 16 shows a plot of the percentage of Ru removed versus Ru concentration for a fixed amount of carbon; the higher the Ru concentration the greater the percentage of Ru that was left in solution, although the amount of Ru adsorbed per gram of carbon increased substantially (FIG. 17). We found that the Ru removal was 34 mg Ru/g carbon at 78% removal from the starting solution. At lower loadings, it is be possible to get >95% Ru removal. As the carbons have a product recovery of 100% (no API removed), it should be understood that one can use greater ratios of carbon to Ru (or carbon to API than we did in these tests) and remove most of the ruthenium.

What is claimed is:

1. A carbon sorbent for removing metals from an active pharmaceutical ingredient (API) organic reaction product, the carbon sorbent comprising:
   (a) a nitrogen content of at least 3 weight %, which is present in the form of pyridine, pyridone, pyrrole or N—P bonds;
   (b) an oxygen content of between 7 weight % and 16 weight %;
   (c) a phosphorous content of at least 0.8 atom % as measured by X-ray photoelectron spectroscopy;
   (d) a BET surface area of between 200 and 1700 meters squared per gram;
   (e) a mesopore volume of at least 0.05 cubic centimeters per gram, wherein mesopores have a diameter of from 2 to 50 nanometers;
   (f) a platinum-group metal uptake of at least 83% from a solution of 1.3 ppm platinum-group metal in an organic solvent with an active pharmaceutical ingredient (API) organic reaction product present in the organic solvent at a concentration of 1.0 grams of the active pharmaceutical ingredient (API) organic reaction product per 0.5 grams of the carbon sorbent, and wherein less than 1% of the active pharmaceutical ingredient (API) organic reaction product is adsorbed by the carbon sorbent from the organic solvent simultaneously with the platinum-group metal uptake;
   wherein the platinum-group metal is-palladium; and,
   (g) a pH of at most 3.1.

2. The carbon sorbent of claim 1, further comprising: an ash content of at most 1.0 weight %.

3. The carbon sorbent of claim 2, further comprising: less than 0.1 atom % Na and less than 0.1 atom % K as measured by X-ray photoelectron spectroscopy.

* * * * *